United States Patent
Yang (10) Patent No.: US 12,400,536 B2
(45) Date of Patent: Aug. 26, 2025

(54) REAL-TIME MONITORING SYSTEM AND METHOD FOR MONITORING EXCRETED BODY FLUID

(71) Applicants: Mikotek Information Inc., Taipei (TW); Ching-Wen Yang, Taipei (TW)

(72) Inventor: Ching-Wen Yang, Taipei (TW)

(73) Assignees: Mikotek Information Inc., Taipei (TW); Ching-Wen Yang, Taipei (TW)

( * ) Notice: Subject to any disclaimer, the term of this patent is extended or adjusted under 35 U.S.C. 154(b) by 109 days.

(21) Appl. No.: 18/472,264

(22) Filed: Sep. 22, 2023

(65) Prior Publication Data

US 2024/0161595 A1    May 16, 2024

(30) Foreign Application Priority Data

Nov. 14, 2022  (TW) .................................. 111143452
Jul. 11, 2023   (CN) .......................... 202310845535.8

(51) Int. Cl.
    *G08B 21/18*    (2006.01)
(52) U.S. Cl.
    CPC .................................. *G08B 21/182* (2013.01)
(58) Field of Classification Search
    CPC .................................................. G08B 21/182
    USPC ........................................................ 340/613
    See application file for complete search history.

(56) References Cited

U.S. PATENT DOCUMENTS

| | | | | |
|---|---|---|---|---|
| 8,797,166 B2 * | 8/2014 | Triener | ................ | A01K 5/0114 340/573.3 |
| 8,981,914 B1 * | 3/2015 | Stetten | ................... | A61B 34/25 340/407.1 |
| 11,540,760 B1 * | 1/2023 | Guillemette | ......... | A47K 13/105 |
| 2009/0149776 A1 * | 6/2009 | Adams | .................. | A61B 5/0059 600/584 |
| 2012/0268278 A1 * | 10/2012 | Lewis | ..................... | A61B 5/002 340/573.5 |
| 2016/0117951 A1 * | 4/2016 | Fleischer | .............. | A61F 5/0059 600/549 |
| 2016/0120455 A1 * | 5/2016 | Pop | ......................... | A61F 13/42 600/301 |
| 2016/0120473 A1 * | 5/2016 | Linton | ................. | A61B 5/6808 600/362 |
| 2018/0110455 A1 * | 4/2018 | Chang | ..................... | A61B 5/208 |
| 2019/0133810 A1 * | 5/2019 | Seres | ..................... | A61B 5/445 |
| 2019/0321587 A1 * | 10/2019 | McMenamin | .... | A61M 25/0017 |
| 2020/0163608 A1 * | 5/2020 | Huang | ............... | A61B 5/14539 |

(Continued)

FOREIGN PATENT DOCUMENTS

| | | |
|---|---|---|
| CN | 201536942 U | 8/2010 |
| CN | 112438730 A | 3/2021 |

(Continued)

*Primary Examiner* — Zhen Y Wu (74) *Attorney, Agent, or Firm* — CKC & Partners Co., LLC (57) ABSTRACT

A fluid real-time monitoring system for monitoring an excreted body fluid of care recipient is provided. The system comprises a weight sensor, a processing device and an alarm device. The weight sensor senses weight information of a fluid collection bag. The processing device coupled to the weight sensor calculates the weight information and generating a first control signal when the weight information is greater than or equal to a critical value of the fluid collection bag. The alarm device coupled to the processing device generates an alarm message according to the first control signal.

14 Claims, 4 Drawing Sheets

(56) References Cited

U.S. PATENT DOCUMENTS

| | | | |
|---|---|---|---|
| 2020/0196933 A1* | 6/2020 | Van Keymeulen | A61B 5/207 |
| 2021/0128368 A1* | 5/2021 | Chan | A61B 5/4318 |
| 2022/0192564 A1* | 6/2022 | Kriscovich | A61B 90/06 |
| 2023/0060232 A1* | 3/2023 | Patel | G16H 40/63 |

FOREIGN PATENT DOCUMENTS

| | | |
|---|---|---|
| JP | 2015-503372 A | 2/2015 |
| JP | 2021-524323 A | 9/2021 |
| JP | 2023-507149 A | 2/2023 |
| TW | M638685 U | 3/2023 |

\* cited by examiner

REAL-TIME MONITORING SYSTEM AND METHOD FOR MONITORING EXCRETED BODY FLUID

CROSS-REFERENCE TO RELATED APPLICATION

This application claims priority to Taiwan Application Serial Number 111143452, filed Nov. 14, 2022, and China Application Serial Number 202310845535.8, filed Jul. 11, 2023, which are herein incorporated by reference.

BACKGROUND OF THE INVENTION

Field of Invention

The present invention relates to a real-time monitoring system, and in particular to a system and method for monitoring excreted body fluid of a care recipient.

Description of Related Art

The fluid collection bag is used to collect the excreted body fluid of the care recipient. If the excreted body fluid is urine, the fluid collection bag is used to collect the urine for patients with dysuria such as urinary incontinence, paraplegia, and long-term bed rest. Generally, the fluid collection bag is composed of a plastic bag, a drainage catheter, a hanging ring, a urine sheath, a drainage tube, and a protective plug. When the patient is unable to urinate on his own or the urine is not clear, a catheter is inserted to the bladder through the urethral opening to drain out the urine.

The fluid collection bag needs to be replaced regularly to avoid infection of the care recipient. Traditionally, whether or not the fluid collection bag is full and whether or not the process of collecting the excreted body fluid of the care recipient is failed are monitored by the medical staff. Such monitoring method increases the burden of the medical staff. Therefore, a fluid real-time monitoring system and method for monitoring the excreted body fluid of the care recipient is needed.

SUMMARY

According to an aspect of the present invention, a fluid real-time monitoring system for monitoring an excreted body fluid of care recipient is provided. The system comprises a weight sensor for sensing a weight information of a fluid collection bag, a processing device electrically connected with the weight sensor for calculating the weight information and generating a first control signal when the weight information is greater than or equal to a critical value of the fluid collection bag, and an alarm device coupled to the processing device for generating an alarm message according to the first control signal.

In some embodiments, the fluid collection bag is a urinary collection bag or an ascites drainage bag.

In some embodiments, the fluid real-time monitoring system further comprises a color detection device electrically connected to the processing device to detect color of fluid in the fluid collection bag, when the processing device determines that the color of the fluid in the fluid collection bag is abnormal, the processing device generates a second control signal to control the alarm device to send out the alarm message.

In some embodiments, the fluid in the fluid collection bag is urine or ascites drainage fluid.

In some embodiments, the fluid real-time monitoring system further comprises a communication device coupled to a remote server, wherein the color of the fluid is transmitted to the remote server to store through the communication device.

In some embodiments, calculating the weight information by the processing device further comprises to calculate a change of the weight information of the fluid collection bag in a time interval to serve as a total amount of fluid excreted in the time interval.

In some embodiments, the fluid real-time monitoring system further comprises a display device for displaying the total amount of fluid excreted in the time interval.

In some embodiments, the weight sensor further comprises a gravity sensor for sensing a motion data of the weight sensor.

In some embodiments, the processing device further determines whether the weight sensor is in a calibration orientation according to the motion data, and when the weight sensor is in the calibration orientation, the processing device controls the weight sensor to perform the automatic zeroing calibration process.

In some embodiments, the processing device further determines whether the weight sensor is in a calibration orientation according to the motion data, and when the weight sensor is in the calibration orientation, the processing device controls the weight sensor to perform a manual calibration.

In some embodiments, the weight sensor has a hook for hanging the fluid collection bag, and the calibration orientation is an orientation of the hook perpendicular to a ground.

In some embodiments, the weight sensor further comprises a positioning device to broadcast a signal with an identification code and the motion data, and a remote server receives the signal to positing the weight sensor according to the identification code and the motion data in the signal.

According to another aspect of the present invention, a fluid real-time monitoring method for monitoring an excreted body fluid is provided. The method comprises sensing a weight information of a fluid collection bag, determining whether the weight information is greater than or equal to a critical value of the fluid collection bag, and generating a first control signal when the weight information is greater than or equal to the critical value of the fluid collection bag to control an alarm device to issue an alarm message.

In some embodiments, the fluid collection bag is a urinary collection bag or an ascites drainage bag.

In some embodiments, the method further comprises detecting color of fluid in the fluid collection bag, determining whether the color of the fluid in the fluid collection bag is normal, and generating a second control signal to control the alarm device to send out the alarm message when the color of the fluid in the fluid collection bag is not normal.

In some embodiments, the fluid in the fluid collection bag is urine or ascites drainage fluid.

In some embodiments, the method further comprises to sense the weight information of the fluid collection bag by a weight sensor.

In some embodiments, the method further comprises to sense a motion data of the weight sensor.

In some embodiments, the method further comprises to determine whether the weight sensor is in a calibration orientation according to the motion data, and controlling the weight sensor to perform the automatic zeroing calibration process when the weight sensor is in the calibration orientation.

In some embodiments, the weight sensor has a hook for hanging the fluid collection bag, and the calibration orientation is an orientation of the hook perpendicular to a ground.

The fluid real-time monitoring system includes a weight sensor to sense the weight of the fluid collection bag in real time. When the weight of the fluid collection bag is greater than or equal to the critical value, the fluid real-time monitoring system may trigger an alarm signal to remind the personnel to check the fluid collection bag to avoid danger. Moreover, the fluid real-time monitoring system also includes a color detection device to detect the color of the excreted body fluid in the fluid collection bag. When the color of the excreted body fluid is abnormal, the fluid real-time monitoring system may trigger an alarm signal to remind the personnel. Therefore, the present application may achieve the effect of real-time monitoring.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

In order to make the above and other objects, features and advantages of the disclosure more comprehensible, several embodiments accompanied with figures are described in detail below.

DETAILED DESCRIPTION

Reference will now be made in detail to the present preferred embodiments of the disclosure, examples of which are illustrated in the accompanying drawings. Wherever possible, the same reference numbers are used in the drawings and the description to refer to the same or like parts.

To comprehensively describe the disclosure in detail, reference may be made to the accompanying drawings and various embodiments. Meanwhile, components and steps known by the public are not described in the embodiments to prevent unnecessary limitations from being imposed to the disclosure.

Terms such as "couple" or "connect" used in the embodiments may refer to two or more components being in physical or electrical contact with each other "directly", two or more components being in physical or electrical contact with each other "indirectly", or acting of two or more components with each other.

The foregoing and other technical content, features, and effects of the present invention can be clearly presented below in detailed descriptions of embodiments with reference to the drawings.

Figure 1:
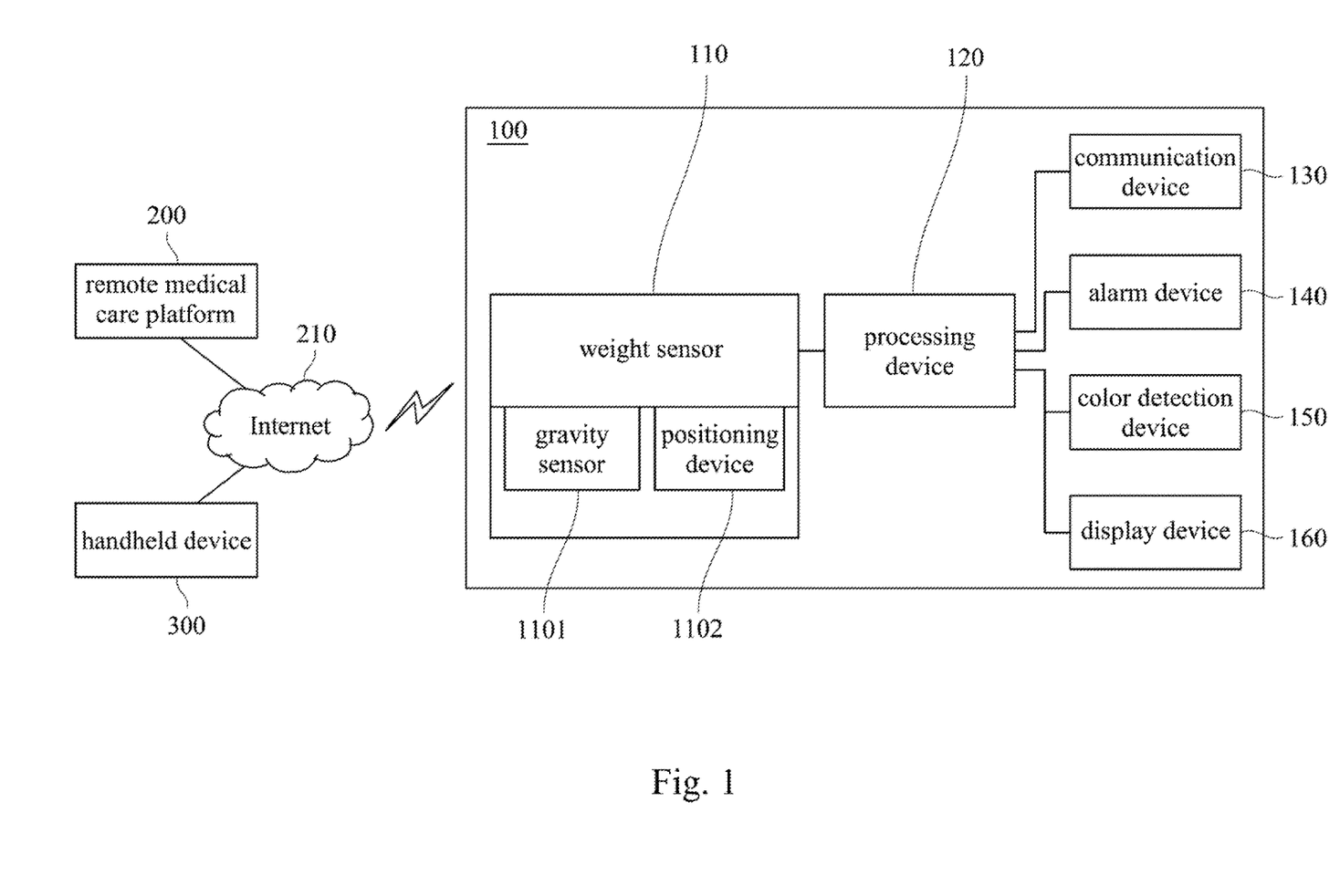
FIG. 1 is a block diagram of a fluid real-time monitoring system for monitoring excreted body fluid of a care recipient according to an embodiment of the present application.

FIG. 1 is a block diagram of a fluid real-time monitoring system for monitoring excreted body fluid of a care recipient according to an embodiment of the present application. As shown in FIG. 1, the fluid real-time monitoring system 100 for monitoring excreted body fluid of a care recipient includes a weight sensor 110, a processing device 120, a communication device 130, an alarm device 140 and a color detection device 150. In one embodiment, the real-time monitoring system 100 can be connected to the Internet 210 through the communication device 130 to connect with the remote medical care platform 200 or the handheld device 300 of the medical staff. Accordingly, the real-time monitoring value monitored by the fluid real-time monitoring system 100 is sent to the remote medical care platform 200 or the handheld device 300 of the medical staff. In one embodiment, the color detection device 150 is installed close to the fluid collection bag to monitor the color of the excreted body fluid in the fluid collection bag in real time. The color of the fluid in the fluid collection bag is used to determine whether there is a care needed state of the care recipient. In one embodiment, the color detected by the color detection device 150 can be transmitted to the database storage in the remote medical care platform 200 or the hand-held device 300 of the medical staff through the communication device 130 in a wireless or wired manner.

In one embodiment, the excreted body fluid includes urine, wound drainage fluid, and ascites drainage fluid. However, this present application is not limited to this. All biological excreted body fluid can be monitored in real time by using the real-time monitoring system 100 of this present application to determine the real time state of the excreted body fluid. In one embodiment, the fluid collection bag is a urinary collection bag if the excreted body fluid monitored by the real-time monitoring system 100 is urine. The fluid real-time monitoring system 100 is used to monitor the weight of the urinary collection bag. In another embodiment, the fluid collection bag is a drainage bag if the excreted body fluid monitored by the fluid real-time monitoring system 100 is the ascites drainage fluid. The fluid real-time monitoring system 100 is used to monitor the weight of drainage collection bag.

In one embodiment, the handheld device 300 of the medical staff is a small portable electronic device, such as a tablet computer, a smart phone, a palmtop computer, or a personal digital assistant. The processing device 120 may be implemented as an integrated circuit, such as a microcontroller, a microprocessor, a digital signal processor, an application specific integrated circuit (ASIC), a logic circuit or other similar circuit or a combination thereof. The communication device 130 can be implemented as a global system for mobile communication (GSM), a personal handy-phone system (PHS), a long term evolution system (LTE), a worldwide interoperability for microwave access (WiMAX), a wireless fidelity (Wi-Fi), and so on. The alarm device 140 can be implemented as a buzzer, a light emitting element or a combination thereof. The alarm device 140 issues a warning sound or flash.

The weight sensor 110 measures the weight of the object to be monitored, such as the weight of a fluid collection bag. In an embodiment, the fluid collection bag is a urinary collection bag or a drainage bag. However, the present invention is not limited thereto. The processing device 120 is electrically connected to the weight sensor 110. The processing device 120 receives the weight of the fluid collection bag measured by the weight sensor 110. When the weight of the urine or ascites drainage fluid contained in the fluid collection bag is about to fill the bag, that is, the weight of the urine or ascites drainage fluid is greater than or equal to the alarm weight, the processing device 120 sends a warning message to the alarm device 140 to issue a warning signal. In one embodiment, the alarm device 140 receives the warning message to issue a warning sound or light. The communication device 130 transmits the weight of the fluid collection bag measured by the weight sensor 110 to the remote medical care platform 200 or the handheld device 300 of the medical staff through the Internet 210 for real-time monitoring. The communication device 130 also receives the setting information sent by the remote medical care platform 200 or the handheld device 300 of the medical staff through the Internet 210 to set the fluid real-time monitoring system 100. The color detection device 150 detects the color of the excreted body fluid in the fluid collection bag. The processing device 120 receives the color of the excreted body fluid detected by the color detection device 150. When the color of the excreted body fluid, such as urine or ascites drainage fluid, is abnormal, the processing device 120 sends a warning message to the alarm device 140 to notify the relevant personnel. The communication device 130 is used to transmit the color of the excreted body fluid, such as the color of urine or ascites drainage fluid, detected by the color detection device 150 to the database storage of the remote medical care platform 200 or the handheld device 300 of the medical staff through the Internet 210 for real-time monitoring or subsequent data extraction. In one embodiment, the remote medical care platform 200 may extract the color data to detect the color change of urine or ascites drainage fluid. In one embodiment, the color detection device 150 is installed at a position near the fluid collection bag to detect the excreted body fluid collected by the fluid collection bag, such as urine or the ascites drainage fluid. The color of the excreted body fluid detected by the color detection device 150 is transmitted to the processing device 120 and automatically uploaded to the database storage in the remote medical care platform 200 in a wired or wireless manner. Such method of automatically uploading the color data may save the time of nursing staff to record the color of the excreted body fluid.

The remote medical care platform 200 or the hand-held device 300 of the medical staff may store the received weight of the fluid collection bag transmitted by the communication device 130. The weight of the fluid collection bag is compared with the alarm weight by the processing device 120 to determine whether the fluid collection bag will be full. When the fluid collection bag is determined to be full, the processing device 120 may notify the personnel to replace or to empty the fluid collection bag. In an embodiment, the alarm weight is a critical value of the fluid collection bag that needs to be replaced or emptied. When the excreted body fluid in the fluid collection bag is greater than or equal to the alarm weight, the processing device 120 may trigger the alarm device 140 to send a warning message to inform the relevant personnel to replace or to empty the fluid collection bag.

Figure 2:
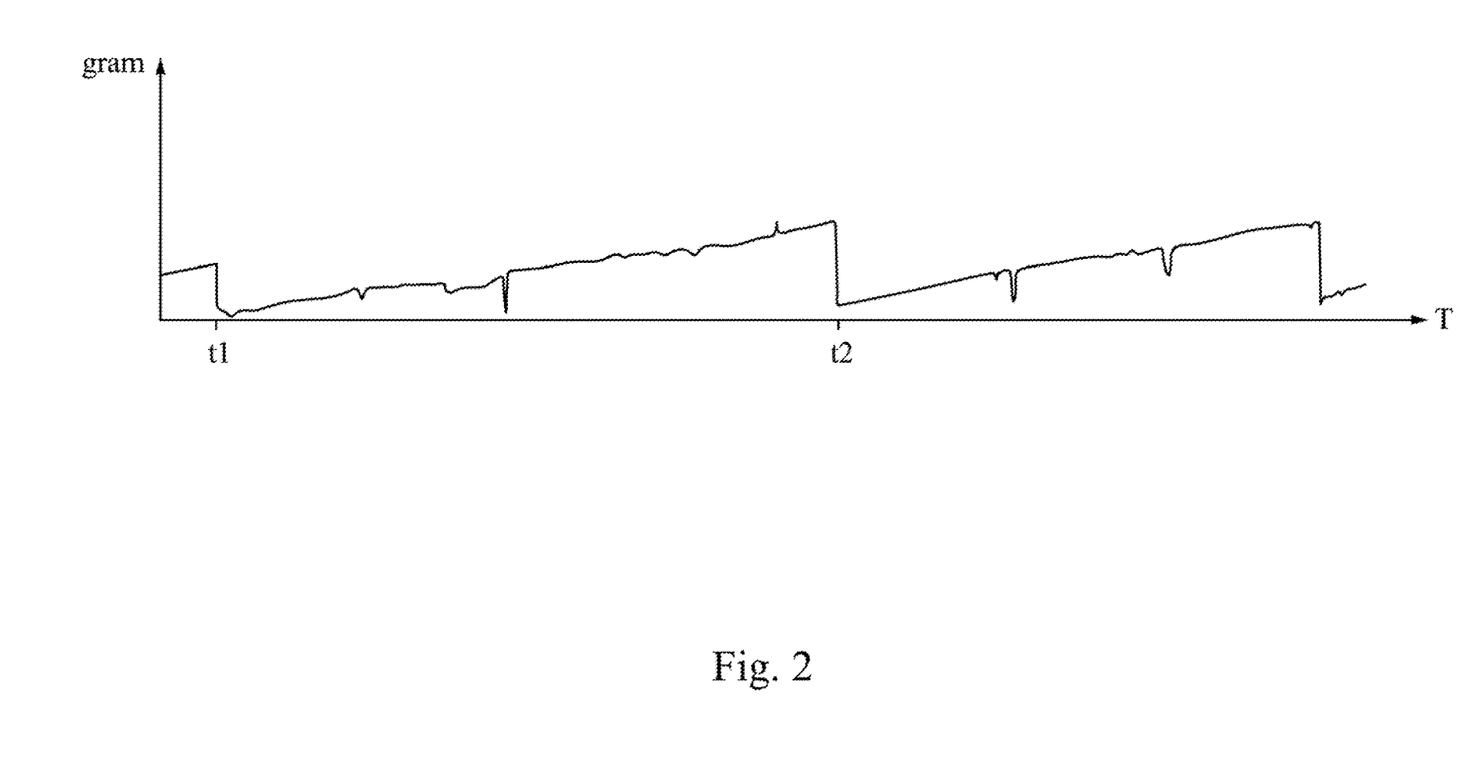
FIG. 2 is a schematic diagram of urine volume of a care recipient according to an embodiment of the present application.

In another embodiment, if the monitored fluid collection bag is a urinary collection bag, the urine volume per unit time of the care recipient is calculated according to the weight of the urinary collection bag measured by the weight sensor 110. The urine volume per unit time of the care recipient is used to determine whether the urine volume of the care recipient is normal. FIG. 2 is a schematic diagram of urine volume of a care recipient. The horizontal axis is time, and the vertical axis is the weight of the urinary collection bag monitored by the fluid real-time monitoring system 100. In one embodiment, the corresponding weight at time t1 is the empty weight of the urinary collection bag that the urine in the urinary collection bag has been emptied. In this embodiment, the empty weight of the urinary collection bag is G1 grams. Because the care recipient may continue to urinate, after t1, the weight of the urinary collection bag monitored by the fluid real-time monitoring system 100 continues to increase until time t2 when the urinary collection bag is emptied again. In this embodiment, the weight measured at time t2 is G2 grams. Accordingly, the processing device 120 subtracts the weight value G1 grams, the weight of the urinary collection bag at time t1, from the highest weight value G2 grams, the weight of the urinary collection bag at time t2, to get the total urine volume output by the care recipient in this time interval, from t1 to t2. In this embodiment, the total urine volume is (G2−G1) grams in this time interval, from t1 to t2.

It is worth noting that the above calculation is the total urine volume output by the care recipient in the time interval, from t1 to t2. However, the time interval can also be set according to the user's needs to evaluate the total urine volume of the care recipient within a unit time, such as every 1 hour, 4 hours, 8 hours, 12 hours or 24 hours. In another embodiment, the remote medical care platform 200 can calculate the urine volume of the care recipient in every 1 hour, 4 hours, 8 hours, 12 hours or 24 hours according to the weight of the urinary collection bag monitored by the weight sensor 110. In this embodiment, the total urine volume calculated by the remote medical care platform 200 can be sent back to the fluid real-time monitoring system 100 to display on the display device 160 of the fluid real-time monitoring system 100, or be sent back to the hand-held device 300 of the medical staff to display on the screen of the hand-held device 300. Accordingly, the clinical nurse or physician can instantly determine whether the urine volume of the care recipient is normal or not.

Figure 3:
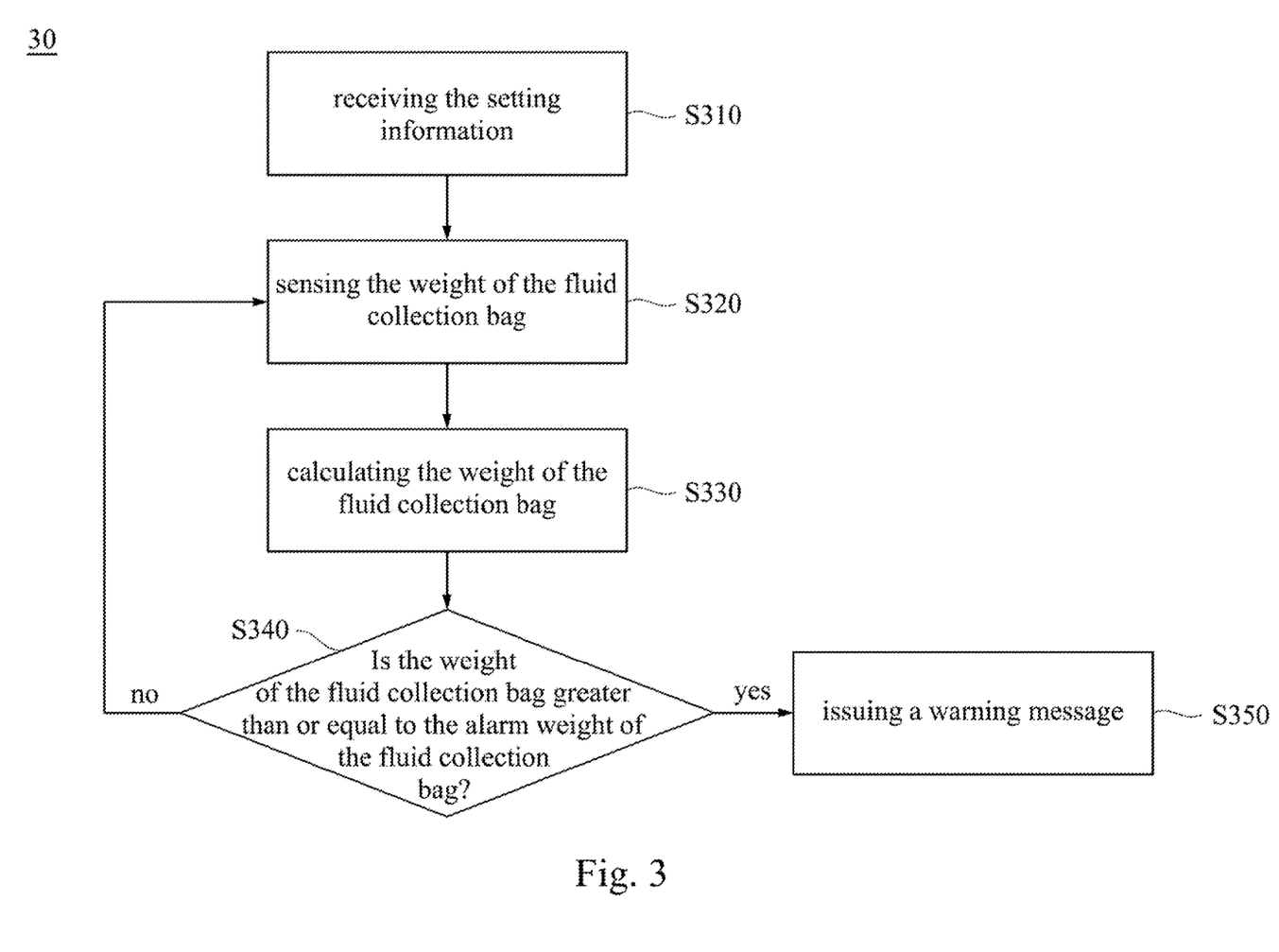
FIG. 3 is a flow chart of a fluid real-time monitoring method for monitoring excreted body fluid of a care recipient according to an embodiment of the present application.

The operation of the fluid real-time monitoring system 100 will be described in detail below with reference to FIG. 1 and FIG. 3. Please refer to FIG. 1 and FIG. 3. FIG. 3 is a flow chart of a real-time monitoring method for monitoring excreted body fluid according to an embodiment of the present application. The real-time monitoring method 30 for monitoring excreted body fluid can be applied to the fluid real-time monitoring system 100 in FIG. 1. The real-time monitoring method 30 for monitoring excreted body fluid includes the following steps. It should be understood that the steps mentioned in this embodiment, unless the order is specifically stated, can be adjusted according to actual needs, and can even be simultaneously or partly simultaneously implement.

In step S310, the processing device 120 receives the setting information sent by the remote medical care platform 200. In one embodiment, the remote medical care platform 200 may store the setting information of different fluid collection bags. The setting information includes the empty weight of the fluid collection bag and the alarm weight of the fluid collection bag that generates the warning information. Therefore, when the user wants to install the fluid collection bag on the fluid real-time monitoring system 100, the processing device 120 downloads the setting information of the corresponding fluid collection bag stored in the remote medical care platform 200 through the Internet 210. The setting information is transmitted to the weight sensor 110 through a wired method. In one embodiment, the fluid collection bag is a urinary collection bag for collecting urine from the care recipient, or a drainage bag for collecting ascites drainage fluid from the care recipient.

In step S320, the weight of the fluid collection bag is sensed by the weight sensor 110 and sent to the processing device 120. Then, in step S330, the weight of the fluid collection bag is calculated by the processing device 120. In one embodiment, when the fluid collection bag is installed on the fluid real-time monitoring system 100, the weight sensor 110 senses the weight of the fluid collection bag and transmits the sensed weight of the fluid collection bag to the processing device 120. The processing device 120 calculates the weight of the fluid collection bag sensed by the weight sensor 110.

In step S340, the processing device 120 determines whether the weight of the fluid collection bag is greater than or equal to the alarm weight of the fluid collection bag. In one embodiment, the processing device 120 determines whether the weight of the fluid collection bag is greater than or equal to the alarm weight of the fluid collection bag according to the weight of the fluid collection bag received from the weight sensor 110. If the weight of the fluid collection bag is not greater than or equal to the alarm weight of the fluid collection bag, the step S320 is performed to continue to sense the weight of the fluid collection bag through the weight sensor 110. If the weight of the fluid collection bag is greater than or equal to the alarm weight of the fluid collection bag, the step S350 is performed to trigger the alarm device 140 to issue a warning message to inform relevant personnel.

In one embodiment, in step S320, the weight of the fluid collection bag is sensed by the weight sensor 110 and sent to the processing device 120. Moreover, the communication device 130 transfers the weight of the fluid collection bag measured by the weight sensor 110 to the database storage in the remote medical care platform 200 or the handheld device 300 of the medical staff for monitoring through the Internet 210. In one embodiment, if the monitored fluid collection bag is a urinary collection bag of the care recipient, the change of the urine volume of the care recipient can be determined through the stored historical weight data. In another embodiment, in step S320, the processing device 120 can further calculate and display the total urine volume of the care recipient in a time interval according to the weight monitored by the weight sensor 110.

On the other hand, the fluid real-time monitoring system 100 further comprises a color detection device 150 for detecting the color of the excreted body fluid in the fluid collection bag. Therefore, step S320 may further detect the color of the excreted body fluid in the fluid collection bag by the color detection device 150 and transmits the color to the processing device 120. Then, in step S340, the processing device 120 receives the color detected by the color detection device 150. When the color of the excreted body fluid in the fluid collection bag is abnormal, the processing device 120 sends a warning message to the alarm device 140 to inform relevant personnel. The communication device 130 transmits the color of the excreted body fluid detected by the color detection device 150 to the remote medical care platform 200 or the hand-held device 300 of the medical staff through the internet 210 for real-time monitoring and recording of the color of the excreted body fluid in the fluid collection bag.

In another embodiment, an automatic zeroing calibration process is performed by the weight sensor 110 in this present application. In one embodiment, if the weight sensor 110 is in a tilted or lying state, or the weight sensor 110 is in a moving or shaking state, these states may affect the zeroing calibration process to result in the calibration weight failure. In order to prevent the weight sensor 110 from performing zeroing calibration process in the above states, the weight sensor 110 further includes a gravity sensor 1101 for sensing motion data of the weight sensor 110. When the processing device 120 performs the automatic zeroing calibration process of the weight sensor 110, the gravity sensor 1101 will first determine whether the motion data of the weight sensor 110 is in the set calibration orientation before performing the zeroing calibration process. In one embodiment, the calibration orientation is the orientation where the hook used to hang the fluid collection bag by the weight sensor 110 is perpendicular to the ground. Accordingly, when the weight sensor 110 is performing the zeroing calibration process, the processing device 120 reads the motion data detected by the gravity sensor 1101 to determine whether the motion data is within the calibration orientation. If the motion data is within the calibration orientation, the processing device 120 control the weight sensor 110 to perform the automatic zeroing calibration process. In contrast, if the motion data is not within the calibration orientation, that is, the hook is not perpendicular to the ground, the processing device 120 prohibits the weight sensor 110 to perform the automatic zeroing calibration process and notifies relevant personnel. In one embodiment, the gravity sensor 1101 is an accelerometer (G-Sensor), a magnetometer (M-Sensor), a gyroscope, a GV-Sensor, a linear acceleration sensor (LA-Sensor), a rotation vector sensor (RV-Sensor), a tilt angle sensor (Tilt-Sensor) or the assembly of the above-mentioned sensors. In an embodiment, the gravity sensor 1101 provides three-axis sensing signals comprising the X-axis acceleration (speed) parameters, the Y-axis acceleration (speed) parameters, and the Z-axis acceleration (speed) parameters.

In another embodiment, when the processing device 120 determine the weight sensor 110 is in an empty state, the processing device 120 control the weight sensor 110 to perform the automatic zeroing calibration process. In another embodiment, when the processing device 120 determines the weight sensor 110 is in an empty state, the operator control the weight sensor 110 to perform the automatic zeroing calibration process. In an embodiment, the empty state means that no fluid collection bag is loaded on the weight sensor 110. In one embodiment, an empty weight value can be set. When the processing device 120 receives the weight sensed by the weight sensor 110 and determines that this weight is less than the empty weight, the processing device 120 determines that the weight sensor 110 is in an empty state, the processing device 120 control the weight sensor 110 to perform the automatic zeroing calibration process.

In one embodiment, the weight sensor 110 is a strain gauge weight sensor. The weight sensor 110 is manually performed a 0-gram calibration process and a 1000-gram calibration process to calculate a corresponding weight formula of the weight sensor 110. When the weight sensor 110 needs to be maintained, the operator can periodically perform the 0-gram calibration process and the 1000-gram calibration process to ensure that the weight calculated by the weight sensor 110 is accurate. Accordingly, before performing the above-mentioned calibration process, the gravity sensor 1101 can be used to determine whether the motion data of the weight sensor 110 is in the calibration orientation. If the motion data of the weight sensor 110 is in the calibration orientation, the above-mentioned calibration process is performed. In other embodiments, different gram calibration processes may be used to calculate a corresponding weight formula of the weight sensor 110. For example, the weight sensor 110 is manually performed a 0-gram calibration process and a 500-gram calibration process to calculate a corresponding weight formula of the weight sensor 110.

Figure 4:
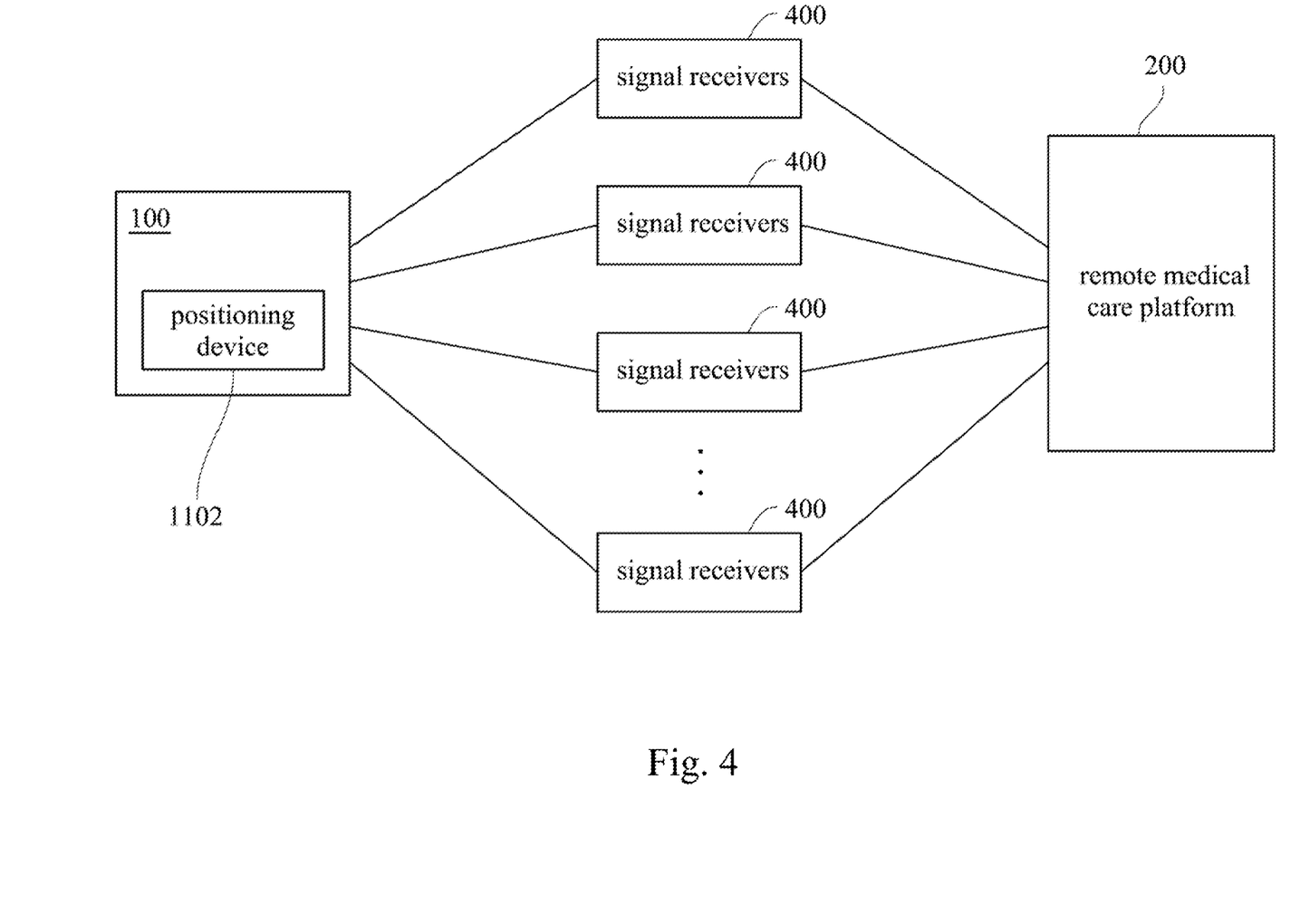
FIG. 4 is a schematic diagram of a positioning system according to an embodiment of the present application.

In another embodiment, the care recipient may move together with the fluid real-time monitoring system 100 on which the fluid collection bag is hung. Therefore, the weight sensor 110 further includes a positioning device 1102 for positioning the care recipient. FIG. 4 is a schematic diagram of a positioning system according to an embodiment of the present application. In a preferred embodiment, if the positioning device 1102 is a Bluetooth signal transmission device, a plurality of signal receivers 400, such as Bluetooth signal receivers, are set at different positions in a medical institution to perform positioning. Each positioning device 1102 of the fluid real-time monitoring system 100 has an identification code. When one of the signal receivers 400 receives the blue-tooth signal of the positioning device 1102, the one of the signal receivers 400 will decode the blue-tooth signal to get the identification code in the blue-tooth signal. The one of the signal receivers 400 will send the identification code to the remote medical care platform 200 to determine the fluid real-time monitoring system 100 based on the identification code. Moreover, the remote medical care platform 200 also determines the position of the fluid real-time monitoring system 100 in the medical institution according to the position of the signal receiver 400 sending the identification code. It should be noted that the above positioning method is only an example and is not intended to limit the implementation of this present application. Other known positioning methods can also be used in this present application to position the fluid real-time monitoring system 100.

In another embodiment, the weight sensor 110 includes a gravity sensor 1101 and a positioning device 1102. The gravity sensor 1101 can sense motion data, such as acceleration, angular acceleration, direction, and movement amount of the fluid collection bag. According to the above motion data, the immediate use status of the fluid collection bag is identified to determine whether the fluid collection bag is dumped or not. Moreover, according to the above motion data, the care recipient's posture is also identified to determine whether the care recipient falls or not. In an embodiment, the positioning device 1102 can simultaneously broadcast identification code and the real-time motion data detected by the gravity sensor 1101 through a blue-tooth signal. The remote medical care platform 200 can determine the position of the care recipient in the medical institution according to the identification code, and determine the care recipient whether falls or not according to the motion data.

As can be seen from the implementation of the above-mentioned embodiment, the fluid real-time monitoring system 100 includes the weight sensor to sense the weight of the fluid collection bag in real time to determine whether or not the weight of the fluid collection bag is greater than or equal to the critical value. When the weight of the fluid collection bag is greater than or equal to the critical value, the fluid real-time monitoring system 100 may trigger an alarm signal to remind the personnel to check the fluid collection bag to avoid danger. Moreover, the fluid real-time monitoring system 100 also includes a color detection device to detect the color of the excreted body fluid in the fluid collection bag. When the color of the excreted body fluid is abnormal, the fluid real-time monitoring system 100 may trigger an alarm signal to remind the personnel. Therefore, the present application may achieve the effect of real-time monitoring and improve the traditional monitoring method of adopting manual monitoring the fluid collection bag. Furthermore, the fluid real-time monitoring system 100 also includes a gravity sensor and a positioning device arranged on the weight sensor. The motion data is sensed by the gravity sensor to determine whether to perform automatic zeroing calibration process or manual calibration process, which may eliminate the disadvantage of performing the above calibration process by the weight sensor in an abnormal orientation. Furthermore, the fluid real-time monitoring system 100 may determine whether an unexpected danger situation has occurred to the care recipient based on the real-time motion data, and to dispatch personnel to the position of the care recipient to take care in real time according to the real-time positioning detected by the positioning device.

The above illustrations contain sequential steps, but these steps do not have to be performed in the order presented. It is within the contemplation of the present disclosure to perform these steps in a different order. These steps may be added, substituted, changed in order and/or omitted as appropriate within the spirit and scope of embodiments of the present disclosure.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. A fluid real-time monitoring system for monitoring an excreted body fluid, comprising:
   a weight sensor for sensing a weight information of a fluid collection bag;
   a processing device, electrically connected with the weight sensor, for calculating the weight information and generating a first control signal when the weight information is greater than or equal to a critical value of the fluid collection bag; and
   an alarm device coupled to the processing device for generating an alarm message according to the first control signal,
   wherein the weight sensor further comprises a gravity sensor for sensing a motion data of the weight sensor, and
   wherein the processing device further determines whether the weight sensor is in a calibration orientation according to the motion data, and when the weight sensor is in the calibration orientation, the processing device controls the weight sensor to perform an automatic zeroing calibration process.

2. The fluid real-time monitoring system according to claim 1, wherein the fluid collection bag is a urine collection bag or an ascites drainage bag.

3. The fluid real-time monitoring system according to claim 1, further comprising a color detection device electrically connected to the processing device to detect color of fluid in the fluid collection bag, when the processing device determines that the color of the fluid in the fluid collection bag is abnormal, the processing device generates a second control signal to control the alarm device to send out the alarm message.

4. The fluid real-time monitoring system according to claim 3, wherein the fluid in the fluid collection bag is urine or ascites drainage fluid.

5. The fluid real-time monitoring system according to claim 3, further comprising a communication device coupled to a remote server, wherein the color of the fluid is transmitted to the remote server to store through the communication device.

6. The fluid real-time monitoring system according to claim 1, wherein calculating the weight information by the processing device further comprising to calculate a change of the weight information of the fluid collection bag in a time interval to serve as a total amount of fluid excreted in the time interval.

7. The fluid real-time monitoring system according to claim 6, further comprising a display device for displaying the total amount of fluid excreted in the time interval.

8. The fluid real-time monitoring system according to claim 1, wherein the weight sensor has a hook for hanging the fluid collection bag, and the calibration orientation is that the hook is perpendicular to a ground.

9. The fluid real-time monitoring system according to claim 1, wherein the weight sensor further comprises a positioning device to broadcast a signal with an identification code and the motion data, and a remote server receives the signal to positing the weight sensor according to the identification code and the motion data in the signal.

10. A fluid real-time monitoring method for monitoring an excreted body fluid, comprising:
    sensing a weight information of a fluid collection bag by a weight sensor;
    determining whether the weight information is greater than or equal to a critical value of the fluid collection bag by a processing device; and
    generating a first control signal by the processing device when the weight information is greater than or equal to the critical value of the fluid collection bag to control an alarm device to issue an alarm message;
    wherein the fluid real-time monitoring method further comprising:
    sensing a motion data of the weight sensor by a gravity sensor in the weight sensor;
    determining whether the weight sensor is in a calibration orientation according to the motion data by the processing device; and
    controlling the weight sensor to perform an automatic zeroing calibration process when the weight sensor is in the calibration orientation.

11. The fluid real-time monitoring method according to claim 10, wherein the fluid collection bag is a urine collection bag or an ascites drainage bag.

12. The fluid real-time monitoring method according to claim 10, further comprising:
    detecting color of fluid in the fluid collection bag;
    determining whether the color of the fluid in the fluid collection bag is normal; and
    generating a second control signal to control the alarm device to send out the alarm message when the color of the fluid in the fluid collection bag is not normal.

13. The fluid real-time monitoring method according to claim 12,
    wherein the fluid in the fluid collection bag is urine or ascites drainage fluid.

14. The fluid real-time monitoring method according to claim 10, wherein the weight sensor has a hook for hanging the fluid collection bag, and the calibration orientation is that the hook is perpendicular to a ground.

* * * * *